(12) United States Patent
Lowe et al.

(10) Patent No.: US 7,220,700 B2
(45) Date of Patent: *May 22, 2007

(54) CATALYST AND PROCESS FOR SELECTIVE HYDROGENATION

(75) Inventors: David M. Lowe, Sunnyvale, CA (US); Michel Molinier, Houston, TX (US); John D. Y. Ou, Houston, TX (US); Michael A. Risch, Seabrook, TX (US); Anthony F. Volpe, Jr., Santa Clara, CA (US); Jeffrey C. Yoder, San Jose, CA (US); Valery Sokolovskii, Sunnyvale, CA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/720,607

(22) Filed: Nov. 24, 2003

(65) Prior Publication Data

US 2005/0113615 A1   May 26, 2005

(51) Int. Cl.
*B01J 23/40*   (2006.01)
*B01J 23/42*   (2006.01)
*B01J 23/56*   (2006.01)

(52) U.S. Cl. .................. 502/325; 502/327; 502/332
(58) Field of Classification Search ................ 502/325, 502/327, 332
See application file for complete search history.

(56) References Cited

U.S. PATENT DOCUMENTS

| 3,651,167 A | 3/1972 | Rosset ................. 260/681.5 |
| 3,793,232 A | 2/1974 | Duhaut et al. |
| 3,859,377 A | 1/1975 | Gross et al. |
| 4,149,961 A | 4/1979 | Antos .................. 208/139 |
| 4,207,169 A | 6/1980 | Courty et al. |
| 4,243,516 A | 1/1981 | Martino et al. |
| 4,420,420 A | 12/1983 | Mita et al. ............. 502/261 |
| 4,487,848 A | 12/1984 | Robinson et al. |
| 4,522,935 A | 6/1985 | Robinson et al. |

(Continued)

FOREIGN PATENT DOCUMENTS

EP   0 261 785   3/1988

(Continued)

OTHER PUBLICATIONS

Li, et al., "Selective Catalytic Reduction of NO Over Metal Oxide or Noble Metal-Doped $In_2O_3/Al_2O_3$ Catalysts By Propene in the Presence of Oxygen", Reaction Kinetics and Catalysis Letters, 2003, vol. 80, No. 1, pp. 75-80, XP008030692.

(Continued)

*Primary Examiner*—J. A. Lorengo
*Assistant Examiner*—Patricia L. Hailey
(74) *Attorney, Agent, or Firm*—Andrew B. Griffis

(57) ABSTRACT

A selective hydrogenation catalyst composition comprises a support; a first metal component comprising rhodium; and a second metal component comprising a metal other than rhodium and selected from Groups 1 to 15 of the Periodic Table of Elements, wherein said first and second components are predominantly contained in an outer surface layer of the support having a depth of not more than 1000 microns.

21 Claims, 1 Drawing Sheet

U.S. PATENT DOCUMENTS

| | | | |
|---|---|---|---|
| 4,691,070 A | 9/1987 | Nakamura et al. | |
| 5,233,118 A | 8/1993 | Bricker et al. | |
| 5,356,851 A | 10/1994 | Sarrazin et al. | |
| 5,364,998 A | 11/1994 | Sarrazin et al. | 585/259 |
| 5,536,695 A | 7/1996 | Blejean et al. | |
| 5,877,363 A | 3/1999 | Gildert et al. | |
| 5,965,481 A | 10/1999 | Durand et al. | 502/304 |
| 6,084,140 A | 7/2000 | Kitamura et al. | |
| 6,096,933 A | 8/2000 | Cheung et al. | |
| 6,153,090 A | 11/2000 | Le Peltier et al. | |
| 6,187,985 B1 | 2/2001 | Le Peltier et al. | |
| 6,255,548 B1 | 7/2001 | Didillon et al. | 585/259 |
| 6,355,854 B1 | 3/2002 | Liu | |
| 6,436,871 B1 | 8/2002 | Liu | |
| 6,486,370 B1 * | 11/2002 | Rende et al. | 585/444 |
| 6,498,280 B1 * | 12/2002 | Uzio et al. | 585/654 |
| 6,503,866 B1 * | 1/2003 | Shepherd et al. | 502/332 |
| 6,514,904 B1 | 2/2003 | Moser et al. | |
| 6,586,647 B1 | 7/2003 | Abrevaya et al. | |
| 6,777,371 B2 | 8/2004 | Liu | |
| 2002/0068843 A1 | 6/2002 | Dai et al. | 585/260 |
| 2002/0136686 A1 | 9/2002 | Takahashi | |

FOREIGN PATENT DOCUMENTS

| | | |
|---|---|---|
| EP | 0 624 399 | 11/1994 |
| WO | WO 98/47617 | 10/1998 |
| WO | WO 98/47618 | 10/1998 |
| WO | WO 98/47620 | 10/1998 |
| WO | WO2004/046076 | 6/2004 |

OTHER PUBLICATIONS

H. Scott Fogler, *Elements of Chemical Reaction Engineering*, 2nd Edition, PTR Prentice Hall, Inc., pp. 29-52 (1992).

J. M. Smith, *Chemical Engineering Kinetics*, McGraw-Hill Book Company, pp. 231-279 (1956).

S. Asplund, "Coke Formation and Its Effect on Internal Mass Transfer and Selectivity in Pd-Catalysed Acetylene Hydrogenation", Journal of Catalysis, vol. 158, pp. 267-278 (1996).

U.S. Appl. No. Awaited, filed Nov. 24, 2003, Lowe et al.

U.S. Appl. No. Awaited, filed Nov. 24, 2003, Molinier et al.

U.S. Appl. No. Awaited, filed Nov. 24, 2003, Lowe et al.

* cited by examiner

CATALYST AND PROCESS FOR SELECTIVE HYDROGENATION

CROSS REFERENCE TO RELATED APPLICATIONS

The present application is related by subject matter to U.S. patent application Ser. No. 10/720,617, filed Nov. 24, 2003 and to U.S. patent application Ser. No. 10/720,558 filed Nov. 24, 2003 filed concurrently herewith, the entire contents of which applications are incorporated herein by reference.

FIELD

This invention relates to a catalyst and a process for the selective hydrogenation of alkynes and diolefins to olefins.

BACKGROUND

Light olefins, such as ethylene, propylene and butylenes, can be produced using various processes such as steam cracking, fluid catalytic cracking, conversion of methanol to olefins, paraffin dehydrogenation, alcohol dehydration, methane coupling and Fischer Tropsch reactions. However, these processes often produce varying levels of acetylenic and/or diene by-products, such as acetylene, methyl acetylene (MA), propadiene (PD), butyne and butadiene. These by-products must be removed from the light olefin streams because they can act as poisons to the downstream processing catalysts, such as polymerization catalysts. The preferred method of removing these by-products is by selective hydrogenation in which, for example, acetylene is converted to ethylene, methyl acetylene and propadiene are converted to propylene, and butyne and butadiene are converted to butylenes.

Currently, the commercial catalysts used for this selective hydrogenation comprise nickel or palladium, such as palladium and silver, on an alumina support. However, in addition to producing the desired olefin products, these catalysts tend to generate significant quantities of saturates (for example, ethane, propane and butanes) as a result of over-hydrogenation and green oil (olefin oligomers) as a result of competing oligomerization reactions. Both of these by-products are undesirable in that they reduce the selectivity to the required light olefins. However, the green oil is particularly problematic in that it decreases the life of the hydrogenation catalyst.

There is therefore a need for an improved catalyst for the selective hydrogenation of alkynes and diolefins, wherein the catalyst exhibits increased olefin selectivity and reduced selectivity to saturates and oligomers, such as green oil, while retaining high hydrogenation activity.

U.S Patent Application Publication No. 2002/0068843 discloses a catalyst for selectively hydrogenating acetylenic and diolefinic compounds with low green oil formation, the catalyst comprising the following active components loaded on a porous inorganic support: (1) at least one of platinum, palladium, nickel, ruthenium, cobalt, and rhodium; (2) at least one of silver, copper, zinc, potassium, sodium, magnesium, calcium, beryllium, tin, lead, strontium, barium, radium, iron, manganese, zirconium, molybdenum, and germanium; (3) at least one rare earth metal selected from scandium, yttrium, and Lanthanides in Group IIIB of Periodic Table of Elements; and (4) bismuth. Preferably, component (1) is platinum or palladium; component (2) is silver, potassium, or sodium; and component (3) is lanthanum or neodymium.

U.S. Pat. No. 6,255,548 discloses a method for selectively hydrogenating a feed comprising an acetylenic compound and/or a diolefin in the presence of a catalyst comprising at least one support, at least one Group VIII metal selected from nickel, palladium, platinum, rhodium, ruthenium and iridium and at least one additional element M selected from germanium, tin, lead, rhenium, gallium, indium, thallium, gold, and silver, wherein the catalyst is formed by introducing said additional element M into an aqueous solvent in the form of at least one water-soluble organometallic compound comprising at least one carbon-M bond. The preferred Group VIII metals are nickel, palladium and platinum and the preferred additional elements M are germanium, tin, gold, and silver.

U.S. Pat. Nos. 5,356,851 and 5,364,998 disclose a catalyst and a process for the selective hydrogenation of unsaturated compounds, wherein the catalyst contains 0.1 to 10% of at least one Group VIII metal selected from nickel, palladium, platinum, rhodium and ruthenium and 0.01 to 10% of at least one Group IIIA metal selected from gallium and indium, the metals being deposited on a support. The preferred Group VIII metals are nickel, palladium and platinum.

Co-pending U.S. patent application Ser. No. 10/720,617, filed Nov. 24, 2003 filed concurrently herewith, describes a catalyst and process for selectively hydrogenating alkynes and/or diolefins, wherein the catalyst comprises support on which is deposited (a) a rhodium component present in an amount such that the catalyst composition comprises less than 3.0% of rhodium by weight of the total catalyst composition; and (b) an indium component present in an amount such that the catalyst composition comprises at least 0.4% and less than 5.0% of indium by weight of the total catalyst composition.

Co-pending U.S. patent application Ser. No. 10/720,558, filed Nov. 24, 2003, describes a catalyst and process for selectively hydrogenating alkynes and/or diolefins, wherein the catalyst comprises a support, at least two different metal components selected from Groups 8 to 10 of the Periodic Table of Elements, and at least one metal component selected from Group 13 of the Periodic Table of Elements. The metal components can be added to the support by impregnation or co-precipitation.

In addition to the types of metal used in the catalyst, the properties of supported catalysts such as those described above may vary significantly depending on the distribution of the metal(s) in the catalysts. For example, the metal(s) may be substantially uniformly distributed throughout the support, can be located within a thin layer at the support surface (commonly referred to as eggshell), can be located at the center of the support (commonly referred to as egg yolk), or can be concentrated between the outer edge and the center of the support (commonly referred to as egg white).

Thus, U.S. Pat. No. 3,859,377 discloses a catalyst for the selective hydrogenation of butadiene that comprises 0.01 to 1 weight % palladium which is at least partially-through or deep-impregnated to a depth of at least 0.12 inch on a kieselguhr support.

In contrast, U.S. Pat. No. 6,096,933 discloses a supported hydrogenation catalyst composition which comprises a palladium component, at least one alkali metal iodide such as, for example, potassium iodide, and an inorganic support material such as alumina, wherein the palladium component is concentrated in an area within about 150 microns of the exterior surface of the composition.

In addition, a supported rhodium catalyst is disclosed in U.S. Pat. No. 4,420,420 in which active rhodium metal is provided on a silica type or titania type support such that the rhodium is present within a depth of about 0.4 mm of the surface of the support. The catalyst optionally contains one or more co-catalysts including alkaline earth metals, such as calcium, magnesium, barium and the like, noble metals, such as platinum, palladium, iridium, ruthenium, gold and the like, iron, nickel, cobalt, cerium and manganese.

Further, U.S. Pat. No. 6,586,647 discloses a catalyst for selectively hydrogenating C4-acetylenes in a liquid hydrocarbon stream containing largely butadiene wherein the catalyst comprises an inorganic oxide support having dispersed thereon finely divided copper metal and an activator metal selected from nickel, cobalt, platinum, palladium, manganese, and a combination thereof where the copper metal and activator metal are dispersed on the support using impregnation where the volume of the impregnating solution is less than that required to fill the pore volume resulting in at least 50 weight % of the copper metal and the activator metal being dispersed on the outer 200 micron layer of the support.

SUMMARY

In one aspect, the present invention resides in a catalyst composition comprising:
(a) a support;
(b) a first metal component comprising rhodium; and
(c) a second metal component comprising a metal other than rhodium and selected from Groups 1 to 15 of the Periodic Table of Elements, wherein said first and second components are predominantly contained in an outer surface layer of the support having a depth of not more than 1000 microns.

Conveniently, the depth of said outer surface layer of the support is not more than 500 microns, for example not more than 300 microns, such as not more than 100 microns.

In one embodiment, said second component comprises indium.

In another aspect, the present invention resides in a catalyst composition comprising:
(a) a support;
(b) a first metal component comprising rhodium;
(b) a second metal component comprising a metal selected from Groups 12 to 15 of the Periodic Table of Elements; and
(c) a third metal component comprising a metal different from those of said first and second components and selected from Groups 1 to 15 of the Periodic Table of Elements, wherein at least said first and second metal components are predominantly contained in an outer surface layer of the support having a depth of not more than 1000 microns.

Conveniently, said third metal component is also predominantly contained in said outer surface layer of the support.

In one embodiment, said third metal component comprises at least one metal selected from Groups 8 to 10 of the Periodic Table of Elements and in particular is selected from one or more of iron, ruthenium and cobalt.

In a further aspect, the invention resides in a method of making a catalyst composition, the method comprising:
(a) applying a rhodium compound to a surface layer of a support having a depth of not more than 1000 microns;
(b) applying a compound of a second metal selected from Groups 12 to 15 of the Periodic Table of Elements to said surface layer of the support; and
(c) applying a compound of a third metal different from rhodium and from said second metal and selected from Groups 1 to 15 of the Periodic Table of Elements to the support.

Conveniently, said third metal compound is applied to the support before either the rhodium compound or the second metal compound.

Conveniently, the second metal compound is applied to the support either concurrently with or before the rhodium compound.

In one embodiment, said second metal is selected from Group 13 of the Periodic Table of Elements, and conveniently is indium.

Conveniently, after (a), and/or (b) and/or (c), the support is calcined at a temperature of about 100° C. to about 600° C.

In yet a further aspect, the invention resides in use of the catalyst compositions described above in a process for selectively removing alkynes and/or diolefins, particularly alkynes and/or diolefins having 2 to 4 carbon atoms, from a feedstock containing olefins, particularly $C_2$ to $C_4$ olefins.

DETAILED DESCRIPTION OF THE EMBODIMENTS

Figure 1:
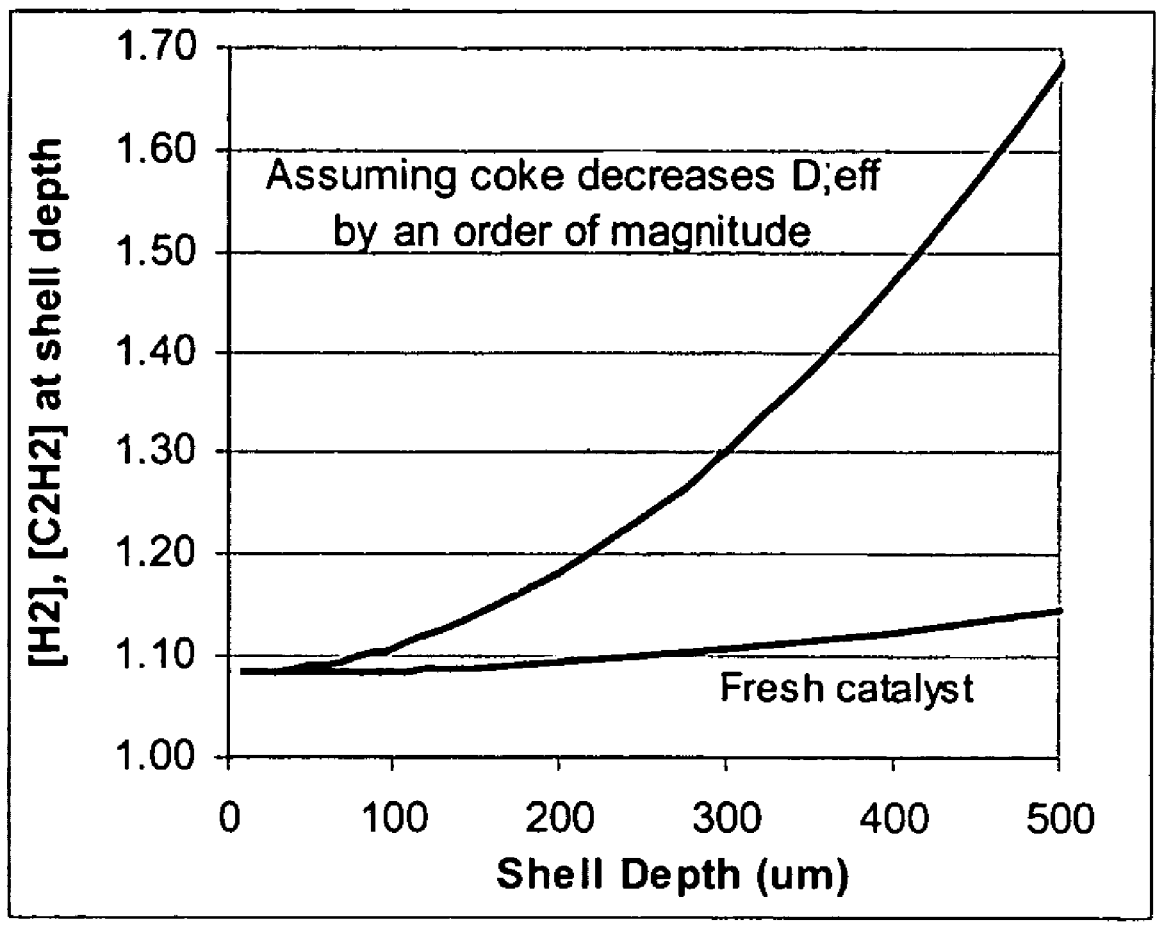
FIG. 1 is a graph plotting hydrogen to acetylene ratio against metal shell depth for a catalyst according to one embodiment of the invention when used in the selective hydrogenation of acetylene.

The present invention relates to a novel catalyst composition, its preparation and its use in the hydrogenation of alkynes and diolefins in a feedstock containing other unsaturated compounds, such as olefins. The catalyst composition comprises a rhodium component and at least one metal component selected from Groups 1 to 15, typically Group 13, of the Periodic Table of Elements other than rhodium, typically indium. The metal components are provided on a support and are applied to the support, generally by impregnation, such that some or all of the metal components are substantially restricted to a surface layer of the support having a depth of not more than 1000 microns, conveniently not more than 500 microns, for example not more than 300 microns, such as not more than 100 microns.

The catalyst composition of the invention is capable of hydrogenating the alkynes and diolefins in the feedstock with high selectivity to olefins and low selectivity to green oil (oligomers) and saturates. An additional benefit of the present catalyst composition is the extension of catalyst lifetime and/or operating cycle due to the reduction in green oil formation.

The Periodic Table of Elements referred to herein is the IUPAC version described in the *CRC Handbook of Chemistry and Physics,* 78th Edition, CRC Press, Boca Raton, Fla. (1997). In addition, the term "component" is used to include a metal compound that may not be purely the elemental metal, but can for example be a sulfide or oxide.

As used herein, the term "acetylene" includes the hydrocarbon $C_2H_2$ as well as other acetylenic hydrocarbons, such as methyl acetylene (MA). The term "ethylene product stream" includes streams containing the hydrocarbon $C_2H_4$ as well as streams containing other mono- and diolefinically unsaturated hydrocarbons. It will be appreciated, however, that while the catalysts are often discussed in terms of selectively hydrogenating acetylene, MA, propadiene (PD)

and optionally, butadiene (BD) in a stream that is predominantly ethylene, propylene and/or butylenes, they are not necessarily limited to the treatment of streams that contain ethylene or propylene or butene, but are expected to find applicability to the selective hydrogenation of other unsaturated compounds in streams of other chemical content as well.

Catalyst Composition

The present catalyst composition comprises a rhodium component and one or more additional metal components located on a support such that at least some of the metal components are concentrated in a surface layer of the support having a depth of not more than 1000 microns, such as not more than 500 microns, for example not more than 300 microns, conveniently not more than 100 microns.

In a first embodiment, the catalyst composition is a bimetallic catalyst including a rhodium component and a second metal component comprising a metal other than rhodium and selected from Groups 1 to 15 of the Periodic Table of Elements, with both the rhodium component and the second metal component being substantially wholly contained within said surface layer of the support. Typically, the second metal component is selected from Group 13 of the Periodic Table of Elements, and more particularly is indium.

The catalyst composition of the first embodiment conveniently comprises from about 0.01% to about 10%, for example from about 0.1% to about 3.0%, such as from about 0.25% to about 2.5%, generally from about 0.3% to about 1.5%, of rhodium by weight of the total catalyst composition and from about 0.01% to about 20%, such as from about 0.4% to about 5.0%, for example from about 0.5% to about 5.0%, by weight of the metal of the second component by weight of the total catalyst composition. Where the second metal is indium, the catalyst composition of the first embodiment conveniently comprises from about 0.01% to about 20%, for example from about 0.4% to about 5.0%, such as from about 0.5% to about 4.0%, generally from about 1.0% to about 3.0%, of indium by weight of the total catalyst composition.

In a second embodiment, the catalyst composition includes:
(a) a first component comprising rhodium;
(b) a second component comprising a metal selected from Groups 12 to 15, such as Group 13, of the Periodic Table of Elements; and
(c) a third component comprising a metal different from those of said first and second components and selected from Groups 1 to 15, such as Groups 8 to 10, of the Periodic Table of Elements, wherein at least the first and second components, and conveniently the first, second and third components, are predominantly contained within said surface layer of the support.

The catalyst composition of the second embodiment conveniently comprises from about 0.01% to about 10%, such as from about 0.04% to about 5%, of rhodium by weight of the total catalyst composition.

The catalyst composition of the second embodiment conveniently comprises from about 0.01% to about 30%, such as from about 0.04% to about 20%, of the metal of second component by weight of the total catalyst composition. Where the second component is indium or an indium compound, the catalyst composition typically comprises from about 0.01% to about 20%, such as from about 0.04% to about 10%, of indium by weight of the total catalyst composition.

The catalyst composition of the second embodiment conveniently comprises from about 0.01% to about 50%, such as from about 0.05% to about 30%, of the metal of the third component by weight of the total catalyst composition. Where the third component is iron or an iron compound, the catalyst composition typically comprises from about 0.05% to about 30%, such as from about 0.1% to about 20%, of iron by weight of the total catalyst composition. Where the third component is cobalt or a cobalt compound, the catalyst composition typically comprises from about 0.05 wt % to about 30 wt %, such as from about 0.1 wt % to about 25 wt %, of cobalt by weight of the total catalyst composition. Where the third component is ruthenium or a ruthenium compound, the catalyst composition typically comprises from about 0.05 wt % to about 10 wt %, such as from about 0.1 wt % to about 5 wt %, of ruthenium by weight of the total catalyst composition.

All weight percentages for the metal components of the catalyst composition are based on the amount of elemental metal present by weight of the total catalyst composition including the support.

In general, the molar ratio of the first component metal to the second component metal is from about 0.1 to about 1.2, such as from about 0.3 to about 0.9, whereas the molar ratio of the first component metal to the third component metal is about 0.001 to about 0.6, such as about 0.002 to about 0.3.

In addition to the active metal components discussed above, the catalyst composition also includes a support or binder material. Suitable support materials comprise amorphous inorganic oxides, such as clays, zirconia, alumina, silica, silica-alumina, ceria-alumina, aluminates (such as aluminates of Groups 1 and 2 and of the Periodic Table of Elements), aluminophosphates, magnesium silicate and magnesium oxide-silicon oxide mixtures, crystalline inorganic oxides, such as spinels, perovskites, and molecular sieves, and other solid inorganic materials, such as carbon, silicon nitride, silicon carbide, boron nitride and metal alloys. Preferred support materials include zirconia, alumina and ceria-alumina. The binder or support material conveniently comprises from about 50 wt % to about 99.9 wt %, such as from about 65 wt % to about 99.5 wt %, of the entire catalyst composition.

In general, the first, second and third components are present in the catalyst composition in elemental form, but one or more of these components may also be present at least partly in other forms, such as the oxide, hydride or sulfide forms.

Method of Making the Catalyst Composition

In making the catalyst composition of the invention, the active metal components can be applied to the desired support using a variety of different procedures, such as impregnation, slurry mixing, precipitation, wash coating and spray coating.

One suitable procedure is by impregnation in which a support, such as alumina, is contacted with an aqueous or organic solution of a compound (such as a nitrate, sulfate, halide, formate, acetate, citrate, oxoacetate, oxalate and acetylacetonate) of the chosen metal or metals, the solution volume being less than, equal to or in excess of the retention volume of the support. After maintaining contact between the support and the solution for about 0.01 to about 24 hours, such as about 0.05 to about 4 hours, the impregnated support is dried and normally calcined. Such a procedure can be used to apply a plurality of active components to the support in a single operation or alternatively separate impregnations can be used to apply the active components successively to the support.

Alternatively, the metal components can be applied to the support by mixing a slurry or solution of a compound of the chosen metal or metals with a slurry of a particulate support in a liquid, such as water. After mixing, the resultant slurry may be treated, such as by heating or vacuum drying, to partially or completely remove the liquid, whereafter the treated support may, if necessary, be filtered, then washed with distilled water, dried and calcined as in the case of the impregnation procedure.

As a further alternative, the metal components can be applied to the support by precipitation. For example, a liquid solution, such as an aqueous solution, comprising a source of ions of one of the active components can be subjected to conditions sufficient to cause precipitation of the component as a solid from solution, such as by the addition of a precipitating reagent to the solution. Conveniently, the precipitation is conducted at a pH above 7. For example, the precipitating agent may be a base such as sodium hydroxide or ammonium hydroxide.

In addition, two or more of the active metal components can be applied to the support simultaneously by co-precipitation. For example, a first liquid solution comprising a source of ions of one of the active components can be combined with a second liquid solution comprising a source of ions of another component. This combination of two solutions can take place under conditions sufficient to cause co-precipitation of both components onto the support from the liquid medium. Alternatively, the source of ions of the one component and the source of ions of the other component may be combined into a single solution. This solution may then be subjected to conditions sufficient to cause co-precipitation of the solid components onto the support, such as by the addition of a precipitating reagent to the solution.

Although any compound of the desired metal can be used to apply the different catalyst components to the support, it is found that in the case of rhodium, the preferred compound used to apply the rhodium to the support is rhodium nitrate. In the case of indium, the preferred compounds are indium nitrate and indium formate. In the case of iron, the preferred compounds are iron nitrate and iron oxalate. In the case of ruthenium, the preferred compound is ruthenium nitrosyl nitrate. In the case of cobalt, the preferred compound is cobalt nitrate.

In addition, although the different catalyst components can be applied to the support in any order and any combination, in the case of the trimetallic catalyst, the third catalyst component is preferably added to the support, such as by impregnation, prior to the addition of either or both of the first and second components. Thereafter, the first and second components can be simultaneously added to the support or the second component can be added to the support before the first component.

Another method of applying the active metal component to the support is by wash or spray coating. Typically this method involves preparing a catalyst powder of known composition, such as by co-precipitation or impregnation of the desired metals on a first support, and then mixing the catalyst powder with a liquid, such as water, to produce a slurry. The slurry is then milled by ball-milling, jet-milling or any other type of milling technique, until the desired particle size in the suspension is obtained. In addition, the pH of the slurry may be adjusted to a desired value, and one or more modifiers, such as a binder and/or a porosity control agent, may be added. Finally, the slurry is applied to a second support (ceramic or inorganic oxide in any kind of commercial support shape such as monolith, spheres, hollow cylinders, stars and the likes) by spraying or dipping or any other type of wash coating technique. The second support can be same as or different from the first support.

It is also possible to employ a combination of methods for applying the metal components to the support. For example, a layer of a highly porous support material, such as colloidal alumina, could be applied to the surface of a less porous support material, such as glass balls, by spray or wash coating and then the desired metal components could be applied to the porous support layer by impregnation or precipitation. Other suitable methods will be evident to those of ordinary skill in the art.

After applying the metal components to the support, the support is normally calcined, such as in air, at between about 100° C. and about 600° C., for example at between about 110° C. and about 500° C. Where the metal components are applied to the support in consecutive steps, a separate calcination step can be conducted after each metal application step or a single calcination step can be conducted after all the metal components have been applied to the support.

Finally, the catalyst composition is conveniently heated in a reducing atmosphere, such as an atmosphere containing about 5 to about 30 mol % hydrogen, with the remainder being an inert gas, such as nitrogen, at a temperature of at least 200° C., such as about 300° C. to about 500° C., to further increase the activity of the catalyst. Such a reduction step can be performed in addition to, or in place of, the calcination step(s) referred to above.

Irrespective of the method of applying the metal components to the support and the subsequent treatment of the catalyst composition, it is important to control the preparation conditions such that the desired metal components are concentrated in a surface layer of the support having a depth of not more than 500 microns. This can be achieved by a variety of methods known in the art including limiting the amount of solvent so as to limit penetration, using diffusion aids to either help metals penetrate deeper or make sure they remain in the outer layer, and controlling the impregnation, drying and/or calcination conditions. Numerous analytical techniques, including but not limited to Scanning Electron Microscopy, Transmission Electron Microscopy, Scanning Transmission Electron Spectroscopy, Energy Dispersive Spectroscopy, X-ray Photoelectron Spectroscopy, Time of Flight Secondary Ion Mass Spectrometry and Microprobe Analysis, can be used to ascertain the distribution of the metal components in the support.

Selective Hydrogenation Process

The catalyst composition of the invention is capable of hydrogenating alkynes and/or diolefins in a feedstock that also contains olefins with high selectivity to olefins and low selectivity to green oil (oligomers formed from two or more alkyne and/or diolefin molecules) and saturates. In particular, when used to selectively hydrogenate $C_2$ to $C_4$ alkynes and/or diolefins in a feedstock also containing $C_2$ to $C_4$ olefins, the present catalyst composition typically achieves an alkyne conversion in excess of 80%, such as in excess of 90%, with an olefin selectivity in excess of 50%, such as in excess of 60%, and a green oil selectivity of less than 10%, such as less than 8%. The reduction in green oil formation should also result in an extension of catalyst lifetime and/or operating cycle.

The selective hydrogenation of acetylene, methyl acetylene (MA), propadiene (PD), and/or butadiene (BD) is typically carried out in one of four unit types:
(a) Front-End Selective Catalytic Hydrogenation Reactors, where the feed is composed of $C_3$ and lighter hydrocarbons, or $C_2$ and lighter hydrocarbons. In the case of raw gas applications, other components such as butadiene, ethyl acetylene, dimethyl acetylene, vinyl acetylene, cyclopentadiene, benzene, and toluene can also be present.
(b) Back-End Selective Catalytic Hydrogenation Reactors, where the feed is composed of an ethylene-rich stream.
(c) MAPD Selective Catalytic Hydrogenation Reactors, where the feed is composed of a propylene-rich stream.
(d) BD Selective Catalytic Hydrogenation Reactors, where the feed is composed of a butylene-rich stream.

The operating parameters of an alkyne/alkadiene selective hydrogenation process are not narrowly critical and can be controlled in view of a number of interrelated factors including, but not necessarily limited to, the chemical composition of the feedstock, the control systems and design of a particular plant, etc. (i.e., different reactor configurations including front-end, tail-end, MAPD, and BD converters as mentioned briefly above). In general, however, suitable operating parameters include a temperature of from about 20° C. to about 150° C., such as from about 30° C. to about 100° C., a pressure of from about 100 psig to about 580 psig (690 kPa to 4100 kPa), such as from about 200 psig to about 440 psig (1400 kPa to 3400 kPa), a $H_2/C_2H_2$ molar feed ratio of from about 1 to about 1000, such as of from about 1.1 to about 800 and, assuming the reaction is in the vapor phase, a GHSV from about 100 to about 20,000, such as from about 500 to about 15,000 or, if the reaction is in the liquid phase, an LHSV of 0.1 to 100, such as from 1 to 25.

The following descriptions serve to illustrate how the inventive process may be practiced in the different commercial units.

In the case of a front-end (FE) selective hydrogenation reactor, the inlet operating temperature may range from about 30 to about 150° C., such as from about 50 to about 100° C. Representative operating pressures may range from about 100 psig to about 500 psig (about 690 to 3,500 kPa), such as from about 200 psig to about 400 psig (about 1400 to 2800 kPa). The GHSV may range from about 5000 to about 20,000, such as from about 8000 to about 15,000. Further, the $H_2$ partial pressure may range from about 25 psig to about 175 psig (about 172 to 1200 kPa), such as from about 50 psig to about 140 psig (about 345 to 965 kPa). The feedstreams in FE selective hydrogenation processes typically contain at least about 20% ethylene, and less than 1% acetylene, with the balance comprising ethane, methane, hydrogen and small amounts of similarly light components. (All percentages are mole % unless otherwise noted). Depending upon the process configuration of the plant, this feed stream can also contain $C_3$ components such as methyl acetylene, propadiene, propylene, and propane. Still heavier components such as 1,3 butadiene; 1,2 butadiene; ethyl acetylene; dimethyl acetylene; vinyl acetylene; cyclopentadiene; benzene; toluene and mixtures thereof may also be present as a result of certain process configurations.

In the case of a back-end selective hydrogenation reactor, the inlet operating temperature may range from about 30 to about 150° C., such as from about 40 to about 90° C. Representative operating pressures may range from about 100 psig to about 500 psig (about 690 to 3500 kPa), such as from about 200 psig to about 400 psig (about 1400 to 2800 kPa). The GHSV may range from about 1000 to about 10,000, such as from about 3000 to about 8000. Further, the $H_2/C_2H_2$ molar feed ratio may range from about 0.5 to about 20, such as from about 1.0 to about 1.5. The feedstreams in back-end selective hydrogenation processes may contain about 2% acetylene, about 70% ethylene, and the balance other $C_2$ compounds.

In the case of a methyl acetylene/propadiene (MAPD) selective hydrogenation reactor, operation can be conducted in either the liquid or vapor phase. In the case of liquid phase operation, the inlet operating temperature may range from about 20 to about 100° C., such as from about 30 to about 80° C. Representative operating pressures may range from about 150 psig to about 600 psig (about 1000 to 4100 kPa), such as from about 250 psig to about 500 psig (about 1700 to 3400 kPa). The LHSV may range from about 0.1 to about 100, such as from about 1 to about 10. In the case of the vapor phase operation, the inlet operating temperature may range from about 20 to about 600° C., such as from about 200 to about 400° C. Representative operating pressures may range from about 150 psig to about 600 psig (about 1000 to 4100 kPa), such as from about 250 psig to about 500 psig (about 1700 to 3400 kPa). The GHSV may range from about 100 to about 20,000, such as from about 500 to about 5000. Further, the $H_2/C_2H_2$ molar feed ratio may range from about 0.5 to about 20, such as from about 1 to about 10. The feedstreams in MAPD selective hydrogenation processes may contain at least 80% propylene, and less than 10% of a compound selected from the group consisting of methyl acetylene, propadiene, and mixtures thereof.

In the case of a butadiene (BD) selective hydrogenation reactor, operation can be conducted in either the liquid or vapor phase. In the case of liquid phase operation, the inlet operating temperature may range from about 20 to about 120° C., such as from about 40 to about 100° C. Representative operating pressures may range from about 150 psig to about 600 psig (about 1000 to 4100 kPa), such as from about 200 psig to about 400 psig (about 1400 to 2800 kPa). The LHSV may range from about 0.1 to about 100, such as from about 1 to about 25. In the case of the vapor phase operation, the inlet operating temperature may range from about 20 to about 600° C., such as from about 50 to about 200° C. Representative operating pressures may range from about 150 psig to about 600 psig (about 1000 to 4100 kPa), such as from about 250 psig to about 500 psig (about 1700 to 3400 kPa). The GHSV may range from about 100 to about 20,000, such as from about 500 to about 5000. Further, the $H_2/C_2H_2$ molar feed ratio may range from about 0.5 to about 20, preferably from about 1 to about 10. The feedstreams in BD selective hydrogenation processes may contain at least 90% butylene, and greater than 0.2% butadiene.

The invention will now be more particularly described with reference to the following Examples and the accompanying drawing.

In the Examples, the following definitions are employed:

$C_2H_2$ Conversion:

$$\frac{(C_2H_2)_{in} - (C_2H_2)_{out}}{(C_2H_2)_{in}} \times 100$$

$C_2H_2$ (Gain) Selectivity:

$$\frac{(C_2H_2)_{in} - (C_2H_2)_{out} - C_2H_{6\ produced} - (2 \times C_{4\ produced} + 3 \times C_{6\ produced})}{(C_2H_2)_{in} - (C_2H_2)_{out}} \times 100$$

-continued $C_2H_6$ Selectivity:

$$\frac{C_2H_6 \text{ produced}}{(C_2H_2)_{in} - (C_2H_2)_{out}} \times 100$$

Green-Oil Selectivity:

$$\frac{(2 \times C_4 \text{ produced}) + (3 \times C_6 \text{ produced})}{(C_2H_2)_{in} - (C_2H_2)_{out}} \times 100$$

EXAMPLE 1

Rh—In—Fe Trimetallic Catalyst

This example illustrates the impact of diffusional constraints in altering the ratios of reactant species contacting a trimetallic catalyst containing 0.4 wt % rhodium, 0.8 wt % indium and 1.2 wt % iron on an alumina support.

The catalyst was prepared as follows. A batch of 1.2 wt % Fe on alumina was first prepared by mixing 40 g of theta-alumina (SBa-90 supplied by Sasol) with 100 mL de-ionized water to produce a slurry and then adding a solution of 3.48 g $Fe(NO_3)_3 9H_2O$ (supplied by Aldrich) dissolved in 40 mL of de-ionized water to the alumina slurry. After stirring for 1 hour, the slurry was gently heated until most of the water was removed. The resulting paste was dried in an oven for 2 hours at 90° C. and the remaining powder was then calcined under air for 2 hours at 120° C. and then for 4 hours at 400° C.

The following day, 20 g of the Fe-containing alumina were mixed with 80 mL de-ionized water to obtain a slurry and 0.56 g 2-amino-2-methyl-1-propanol (supplied by Avocado) was added to the slurry. Separately, 0.26 g $Rh(NO_3)_3$ $2H_2O$ (supplied by Alfa) and 0.42 g $In(NO_3)_3 H_2O$ (supplied by Alfa), were dissolved in 160 cc $H_2O$. The Rh and In containing solution was then added to the slurry solution and stirred for 1 hour. After 1 hour, the slurry was heated gently to evaporate the solvent while stirring. The recovered solid was then dried in an oven for 4 hours at 90° C., then calcined in a furnace according to the following procedure: 1 hour ramp to 120° C., 2 hours at 120° C., 2 hours ramp to 450° C., 4 hours at 450° C., under air flow.

The catalyst was used as a powder sized to 20×40 mesh size (~0.6 mm) and was pre-reduced at 450° C. for 5 hours under 100% $H_2$. The catalyst was evaluated in the reduction of a hydrocarbon feed under the following conditions: Temperature (T)=100° C., Pressure (P)=300 psig, GHSV=4500, $H_2/C_2H_2$ feed ratio=1.1. The hydrocarbon feed contained nominally 1.65 mole % acetylene and 70 mole % ethylene, with balance being nitrogen. Impurities that may be present in the feed include carbon monoxide (<0.5 ppm), mercury, arsine, phosphorus (<5 ppb), sulfur (<1 ppm), oxygen (<1 ppm), water (<10 ppm), acetone (<10 ppm) and methanol (<2 ppm). Test results are given in Table 1 below.

TABLE 1

| Catalyst (wt %) | $C_2H_2$ conv (%) | $H_2$ conv (%) | $C_2H_4$ select (%) | $C_2H_6$ select (%) | Green Oil select (%) |
|---|---|---|---|---|---|
| 0.4% Rh/0.8% In/1.2% Fe | 99.9 | 100 | 77.2 | 17 | 5.8 |

Assuming 1st order reactions in both $H_2$ and $C_2H_2$, approximate kinetic rate constants for the disappearance of $H_2$ and $C_2H_2$ are calculated according to methods in *Elements of Chemical Reaction Engineering*, H. S. Fogler, 1992, P T R Prentice-Hall, Inc., p29-52. Theoretical effective diffusivities are calculated according to the methods in *Chemical Engineering Kinetics*, J. M Smith, 1956, McGraw-Hill Book Company, p231-279, assuming 100A pores in the catalyst support. Table 2 below lists the relative values of effective diffusivities and approximate 1st order rate constants for $H_2$ and $C_2H_2$.

TABLE 2

|  | Hydrogen:Acetylene |
|---|---|
| Effective Diffusivity | 4.3 |
| Approximate 1st Order Rate Constant | 1.0 |

FIG. 1 illustrates how $H_2/C_2H_2$ ratios change as a function of depth of the catalyst eggshell on a fresh catalyst. The ratios were calculated from acetylene and hydrogen profiles obtained by solving a reaction-diffusion equation in one dimension (assuming the curvature of the catalyst sphere is large compared to the thickness of the shell). Experimental approximate rate constants and theoretical diffusivities as explained above were utilized in the calculation. Also included are the $H_2/C_2H_2$ ratios as a function of depth of the catalyst eggshell assuming that the effective diffusivities are an order of magnitude lower than the theoretically calculated values in the table above. The presence of coke formed during reaction has been shown to lower effective diffusivities. Asplund (*J. Cat.* 158 267-278 (1996)) has measured effective diffusivities on coked Pd-based catalysts in acetylene hydrogenation service to be an order of magnitude lower than on fresh catalyst.

The higher effective diffusivity of $H_2$ versus $C_2H_2$ combined with the similar approximated first-order rate constants for the disappearance of the two species contribute to the change of the reactant feed ratio within the catalyst particle. For example, under the assumptions described above, it can be seen from FIG. 1 that the reactant ratio begins to exceed the feed ratio after a depth of approximately 200 μm within the fresh catalyst eggshell. In addition, if diffusivities are lower than those calculated theoretically, a more drastic effect is observed and the ratio of $H_2/C_2H_2$ within the eggshell starts to increase beyond the feed ratio at a depth of approximately 50 μm. For an eggshell depth of 300 μm under these conditions, the $H_2/C_2H_2$ ranges from 1.08 to 1.3 within the shell.

EXAMPLE 2

Rh—In—Fe Catalyst

This example illustrates the adverse effect of olefin selectivity loss resulting from higher $H_2/C_2H_2$ ratios with a trimetallic catalyst containing 0.3 wt % rhodium, 0.6 wt % indium and 5.0 wt % iron on an alumina support.

The catalyst was prepared on ~3 mm theta-alumina spheres (supplied by Sasol) as follows. Three 10 g batches of 5 wt % Fe on alumina were first prepared by dissolving 10.8 g of $Fe(NO_3)_3 9H_2O$ (supplied by Aldrich) in 24 mL of de-ionized $H_2O$, dividing the solution into three 8 mL aliquots and delivering the aliquots to separate 10 g of batches of theta-alumina via a spray bottle to achieve incipient wetness. Each batch was then calcined in a furnace according to the following procedure: 1 hour ramp to 120° C., 2 hours at 120° C., 2 hours ramp to 450° C., 4 hours at 450° C., under air flow.

The following day, 0.28 g of Rh(NO$_3$)$_3$2H$_2$O (supplied by Alfa) and 0.50 g In(NO$_3$)$_3$H$_2$O (supplied by Alfa) were dissolved in 24 mL de-ionized H$_2$O. 8 mL of solution were delivered by spray bottle to each 10 g batch of 5 wt % Fe on alumina prepared previously. Each batch was then calcined a second time in a furnace according to the following procedure: 1 hour ramp to 120° C., 2 hours at 120° C., 2 hours ramp to 450° C., 4 hours at 450° C., under air flow. The three batches were subsequently combined and mixed well to achieve a single large batch of catalyst with the same nominal metals composition.

The catalyst was tested under the same conditions as those in Example 1, except for the H$_2$/C$_2$H$_2$ ratio which is noted in Table 3 below.

TABLE 3

| H$_2$/C$_2$H$_2$ feed ratio | C$_2$H$_2$ conv (%) | H$_2$ conv (%) | C$_2$H$_4$ select (%) | C$_2$H$_6$ select (%) | Green Oil select (%) |
|---|---|---|---|---|---|
| 1.1 | 69.5 | 83.5 | 50.7 | 43.4 | 5.9 |
| 1.36 | 69.7 | 86.6 | 13 | 79.2 | 7.9 |

It is seen that at approximately constant acetylene conversion, the higher H$_2$/C$_2$H$_2$ feed ratio leads to over-hydrogenation and a loss in ethylene selectivity, decreasing from 50.7% to 13%, as well as an increase in green oil selectivity.

EXAMPLE 3

Rh—In—Fe Catalysts

This example illustrates the advantage of having the catalytically active material effectively located in the outer shell of a spherical support as compared with being distributed throughout the sphere.

Catalyst A was prepared on 2.5 mm alumina spheres (Sasol, alumina spheres 2.5/210, pre-calcined at 975° C.) as follows. A 20 g batch of 1.2 wt % Fe on alumina was first prepared by dissolving 1.74 g of Fe(NO$_3$)$_3$9H$_2$O (supplied by Aldrich) in 20 mL of de-ionized H$_2$O and then spraying the solution onto the alumina spheres in a rotary tumbler while the tumbler was rotating. The spheres were then dried at room temperature under vacuum, and finally calcined in a furnace according to the following procedure: 1 hour ramp to 120° C., 2 hours at 120° C., 2 hour ramp to 400° C. and 4 hours at 400° C., under air flow.

The following day, 0.25 g of Rh(NO$_3$)$_3$2H$_2$O (supplied by Alfa) and 0.42 g In(NO$_3$)$_3$H$_2$O (supplied by Alfa) were dissolved in 20 mL of de-ionized H$_2$O and the resultant solution was sprayed onto the 20 g batch of 1.2 wt % Fe-impregnated alumina spheres in a rotary tumbler while the tumbler was rotating. The spheres were dried at room temperature under vacuum, and finally calcined in a furnace according to the following procedure: 1 hour ramp to 120° C., 2 hours at 120° C., 2 hour ramp to 400° C. and 4 hours at 400° C., under air flow.

Some spheres of catalyst A were cut open and examined. It appeared that the metals had been impregnated throughout the catalyst spheres since no color gradient was observable.

Catalyst B was prepared using the 0.4 wt % Rh 0.8 wt % In 1.2 wt % Fe on alumina powder described in Example 1. Thus, 7 g of catalyst powder were ball milled with 25 mL de-ionized water for 6.5 hours and the pH of the resulting sol was adjusted by adding 0.4 mL of 3NHNO$_3$. Thereafter 1.84 g of a colloidal alumina binder (Nyacol AL-20, obtained from PQ Corporation) and 0.42 g of cellulose (Avicel, obtained from FMC Corporation) were added to the sol. The sol was then sprayed onto alumina spheres (Condea, alumina spheres 2.5/210, pre-calcined at 1200° C.), such that the total loading of sprayed material was 660 mg/g of alumina spheres. The material was then dried at 120° C. for 4 hours and calcined at 450° C. for 4 hours. The rhodium loading per volume of the resulting material was 1.1 mg/mL.

Some spheres of catalyst B were cut open and examined. Metal coloration was confined to the outer surface of the catalyst spheres, indicating that the metals were restricted to the surface shell of the catalyst. The calculated shell thickness was 288 μm.

Catalysts A and B were tested under the same conditions as those in Example 1. The charge of catalyst B was adjusted to account for the higher metal loading of catalyst A, so that the same amount of catalytically active material (that is, rhodium-indium-iron) was present in the reactor during these two tests. The results are depicted in Table 3 below.

TABLE 3

| Catalyst | C$_2$H$_2$ conv (%) | H$_2$ conv (%) | C$_2$H$_4$ select (%) | C$_2$H$_6$ select (%) | Green Oil select (%) |
|---|---|---|---|---|---|
| A | 73.5 | 91.5 | 48.8 | 44 | 7.2 |
| B | 87.8 | 99 | 73.7 | 19.7 | 6.5 |

It is seen that in the case where the metals are deposited in a <300 μm shell fashion (i.e. impregnated powder deposited on spheres, catalyst B), a substantial gain in acetylene conversion and ethylene selectivity is obtained as compared with the case where spheres are impregnated directly with the metals without any shell thickness control (catalyst A).

While the present invention has been described and illustrated by reference to particular embodiments, those of ordinary skill in the art will appreciate that the invention lends itself to variations not necessarily illustrated herein. For example, it is within the scope of this invention to produce a catalyst composition comprising four or more different metal components. For this reason, reference should be made solely to the appended claims for purposes of determining the true scope of the present invention.

The invention claimed is:

1. A catalyst composition consisting of:
   (a) a support;
   (b) rhodium component;
   (c) an indium component; and optionally
   (d) a third metal component wherein the metal in said third metal component is selected from the group consisting of iron, cobalt, and ruthenium,
wherein said rhodium and indium components and said third metal component, if present, are predominantly contained in an outer surface layer of the support having a depth of not more than 300 microns.

2. The catalyst composition of claim 1 wherein the depth of said outer surface layer of the support is not more than 100 microns.

3. The catalyst composition of claim 1, wherein rhodium is present in the amount of from about 0.01% to about 10% by weight of the total catalyst composition including the support.

4. The catalyst composition of claim 1, wherein rhodium is present in the amount of from about 0.04% to about 5% by weight of the total catalyst composition including the support.

5. The catalyst composition of claim 1, wherein indium is present in the amount of from about 0.01 wt % to about 30 wt % by weight of the total catalyst composition including the support.

6. The catalyst composition of claim 1, wherein indium is present in the amount of from about 0.04 wt %, to about 20 wt % by weight of the total catalyst composition including the support.

7. The catalyst composition of claim 1, wherein rhodium is present in the amount of from about 0.04% to about 10% by weight of the total catalyst composition including the support.

8. The catalyst composition of claim 1, wherein the metal in said third metal component is present in the amount of from about 0.01% to about 50% by weight of the total catalyst composition including the support.

9. The catalyst composition of claim 1, wherein the metal in said third metal component is present in the amount of from about 0.05% to about 30% by weight of the total catalyst composition including the support.

10. The catalyst composition of claim 1 wherein the metal in said third metal component is iron present in the amount of from about 0.05% to about 30% by weight of the total catalyst composition including the support.

11. The catalyst composition of claim 1 wherein the metal in said third metal component is iron present in the amount of from about 0.1% to about 20% by weight of the total catalyst composition including the support.

12. The catalyst composition of claim 1 wherein the metal in said third metal component is cobalt present in the amount of from about 0.05% to about 30% by weight of the total catalyst composition including the support.

13. The catalyst composition of claim 1 wherein the metal in said third metal component is cobalt present in the amount of from about 0.1% to about 25% by weight of the total catalyst composition including the support.

14. The catalyst composition of claim 1 wherein the metal in said third metal component is ruthenium present in the amount of from about 0.05% to about 10% by weight of the total catalyst composition including the support.

15. The catalyst composition of claim 1 wherein the metal in said third metal component is ruthenium present in the amount of from about 0.1% to about 5% by weight of the total catalyst composition including the support.

16. A method of making a catalyst composition according to claim 1, the method comprising:
   (a) applying a rhodium compound to a surface layer of a support having a depth of not more than 300 microns;
   (b) applying an indium compound to a surface layer of the support having a depth of not more than 300 microns; and optionally
   (c) applying a compound of a third metal selected from the group consisting of iron, cobalt, and ruthenium to a surface layer of the support having a depth of not more than 300 microns.

17. The method of claim 16 wherein said third metal compound is applied to the support before either the rhodium compound or the indium compound.

18. The method of claim 16 wherein the indium compound is applied to the support either concurrently with or before the rhodium compound.

19. The method of claim 16 wherein at least one of (a), (b) and (c) is effected by an impregnation, precipitation, slurry mixing or coating step.

20. The method of claim 16 and, after (a) and/or (b) and/or (c), calcining the support at a temperature of about 100° C. to about 600° C.

21. The method of claim 16 and, after (a), (b) and (c), treating the calcined support in a reducing atmosphere at a temperature in excess of 200° C.

* * * * *